United States Patent
Xu

(10) Patent No.: US 10,288,562 B2
(45) Date of Patent: May 14, 2019

(54) LIGHT REFLECTION IMAGING METHOD FOR ACQUIRING OPTICAL PARAMETERS AND MICROSTRUCTURES OF TISSUES IN A LARGE AREA

(71) Applicant: WENZHOU MEDICAL UNIVERSITY, Wenzhou, Zhejiang (CN)

(72) Inventor: Min Xu, Sunnyside, NY (US)

(73) Assignee: WENZHOU MEDICAL UNIVERSITY, Wenzhou, Zhejiang (CN)

( * ) Notice: Subject to any disclaimer, the term of this patent is extended or adjusted under 35 U.S.C. 154(b) by 0 days.

(21) Appl. No.: 15/768,445

(22) PCT Filed: Oct. 29, 2015

(86) PCT No.: PCT/CN2015/093184
§ 371 (c)(1),
(2) Date: Apr. 13, 2018

(87) PCT Pub. No.: WO2017/063236
PCT Pub. Date: Apr. 20, 2017

(65) Prior Publication Data
US 2018/0321148 A1    Nov. 8, 2018

(30) Foreign Application Priority Data
Oct. 15, 2015    (CN) .......................... 2015 1 0666945

(51) Int. Cl.
*G01N 21/47*    (2006.01)
*G01N 21/55*    (2014.01)
*A61B 5/00*    (2006.01)

(52) U.S. Cl.
CPC ............... *G01N 21/55* (2013.01); *A61B 5/00* (2013.01); *A61B 5/0075* (2013.01);
(Continued)

(58) Field of Classification Search
CPC ............ G01N 21/4795; G01N 21/4738; A61B 5/14532; A61B 5/14546; A61B 5/1455;
(Continued)

(56) References Cited

U.S. PATENT DOCUMENTS

| 6,615,061 B1 * | 9/2003 | Khalil ............... G01N 21/49 600/310 |
| 2002/0026106 A1 * | 2/2002 | Khalil ............... A61B 5/14532 600/310 |

(Continued)

FOREIGN PATENT DOCUMENTS

CN         101856219 A    10/2010

OTHER PUBLICATIONS

Reilly, Michael, et al., "Analytical model for sub-diffusive light reflection and the application to spatial frequency-domain imaging," *Proc. of SPIE*, vol. 9319, pp. 93191A-1-93191A-6 (Mar. 12, 2015).

(Continued)

*Primary Examiner* — Isiaka O Akanbi
(74) *Attorney, Agent, or Firm* — Christensen, Fonder, Dardi & Herbert PLLC

(57) ABSTRACT

A light reflection imaging method for acquiring optical parameters and microstructures of tissues in a large area, comprising a turbid medium reflectance calculation method applicable at a random spatial distance and in an entire spatial frequency domain, and a method of measuring the reflectance of a turbid medium at high and low spatial frequencies and inverting the obtained light reflectance to obtain optical parameters of the medium. The inversion method may be a table lookup method or a formula fitting method. The measurement of sub-diffuse and diffuse light reflectance of the turbid medium can be used for measuring the optical properties of the turbid medium and microstructures including a phase function and the like in a large area.

9 Claims, 12 Drawing Sheets

(52) U.S. Cl.
CPC ..... *G01N 21/4738* (2013.01); *G01N 21/4795* (2013.01); *A61B 5/0059* (2013.01)

(58) Field of Classification Search
CPC ............ A61B 5/1491; A61B 2562/043; A61B 5/0075; A61B 5/6824; A61B 2562/0233; A61B 2562/0242
USPC .......................... 356/334–338, 445–446, 369
See application file for complete search history.

(56) References Cited

U.S. PATENT DOCUMENTS

| | | |
|---|---|---|
| 2004/0030255 A1 | 2/2004 | Alfano et al. |
| 2005/0073681 A1* | 4/2005 | Sevick-Muraca ............................ G01N 15/0205 356/336 |
| 2015/0276571 A1* | 10/2015 | Hajjarian ............... G01N 21/41 73/54.02 |

OTHER PUBLICATIONS

Xu, Lanqing, et al., "Discussion on backscattered photon numbers and their scattering events in a turbid media," *ACTA Physica Sinica*, vol. 57, No. 9, pp. 6030-6035 (Sep. 15, 2008).

* cited by examiner

LIGHT REFLECTION IMAGING METHOD FOR ACQUIRING OPTICAL PARAMETERS AND MICROSTRUCTURES OF TISSUES IN A LARGE AREA The present application is a National Phase entry of PCT Application No. PCT/CN2015/093184, filed Oct. 29, 2015, which claims the benefit of Chinese Patent Application No. 201510666945.1, filed Oct. 15, 2015, which are incorporated herein by reference.

TECHNICAL FIELD

The present disclosure provides a light reflection imaging method for acquiring optical parameters and microstructures of tissues in a large area, which can be used in the fields of biomedical optics, remote sensing and the like.

BACKGROUND

Elastic scattering of light has long been used for analyzing random media. Reflectance spectroscopy and imaging are widely used noninvasive methods for measuring the optical properties of random media (e.g., atmosphere, oceans and tissues), including an absorption coefficient ($\mu_a$) and a reduced scattering coefficient ($\mu_s'$). These parameters can provide valuable information about the microstructures and the biochemical components of the media, and have been applied in the fields of cloud remote sensing, monitoring of cell apoptosis, skin characterization, cancer detection and the like. Since radiative transfer (RT) describes the propagation of light in random media, the reflectance of scattered light is essentially a difficult problem. Particularly in the case of a short light source-detector distance, the diffusion approximation usually adopted for the RT cannot work. Therefore, it is still difficult to quantify a phase function of a medium from reflectance measurement, particularly to acquire a medium phase function containing basic information of a microenvironment of the relevant medium. In the case of a random light source-detector distance, an accurate analysis model for reflectance is highly desirable. This model will be applied to rapid quantitative evaluation on optical properties, especially on a phase function of a random medium. Those reflectance empirical models in the case of a short light source-detector distance proposed recently have respective limitations. Since the phase function of the scattering medium has a significant influence on the sub-diffuse reflection in the case of a short light source-detector distance, an explicit analysis model that is related to the relation between the sub-diffuse reflectance and the phase function and can deduce the optical parameters (including the phase function) of the random medium from the reflectance distribution is extremely desirable.

SUMMARY

The present disclosure relates to a light reflection imaging method for acquiring optical parameters and microstructures of tissues in a large area. The core of the method is to combine small-angle approximation (SAA) of radiative transfer to give a quantitative analysis relation between a near distance sub-diffuse scattering light reflectance and a scattering medium phase function.

The present disclosure provides a light reflection imaging method for acquiring optical parameters and microstructures of tissues in a large area, according to $$I(q) = \begin{cases} I_{snake}(q) + I_{diffuse}(q) + \mu_b/2\mu_t & q < q_c \\ I_{SAA}(q) & q > q_c \end{cases},$$

respectively obtaining a low-frequency reflectance formula $$I_{snake}(q) + I_{diffuse}(q) + \mu_b/2\mu_t$$

and a high-frequency reflectance formula $$I_{SAA}(q),$$

wherein $q_c \sim 2\pi\beta$, obtaining an absorption coefficient $\mu_a$ and a reduced scattering coefficient $\mu_s'$ from the obtained reflectance through the low-frequency reflectance formula and an inversion method in sequence, and obtaining an anisotropic factor g, a propagation length scale $l_\theta$ and an isotropic scattering background $p_b$ of a random phase function of a scattering medium with the inversion method through the high-frequency reflectance formula.

The inversion method is a table lookup method or a formula fitting method.

The high-frequency reflectance formula $$I_{SAA}(q) = \int_0^\infty dz \mu_b(z) \times \left[ S^{eff}(q,z;s_\perp) + \frac{2p_{iso}}{1-p_{iso}} S^{eff'}(q,z;s_\perp) \right]$$

is obtained from an SAA diffusion function $$S(q,z;s_{\perp 0}) = \exp(-iq \cdot s_{\perp 0} z)\exp[-\int_0^z \mu_t(z-\zeta)d\zeta + \int_0^z \mu_s(z-\zeta) \chi(q\zeta,z-\zeta)d\zeta]$$

Assuming that $p_{Forward}(\theta)$ satisfies Gaussian distribution, the random phase function $p(\theta)$ of the scattering medium is modified into:

$$p_{SAA}(\theta) = \frac{1-2p_b}{\pi\Theta^2}\exp\left(-\frac{\theta^2}{\Theta^2}\right) + \frac{1}{2\pi}p_b,$$

from which $$p_b = 2\pi \int_{\pi/2}^\pi p(\theta)\sin\theta d\theta \text{ and}$$

$$\theta^2 = \frac{2\pi}{1-2p_b}\int_0^\pi p(\theta)\theta^2 \sin\theta d\theta$$

are obtained, through $p_{iso}=2p_b$, the SAA diffusion function is transformed into $$S(q,z;s_{\perp 0}) = \exp(-iq \cdot s_{\perp 0} z)\exp\left[-\mu_t z + (1-2p_b)\mu_s \sqrt{\pi} \frac{\text{erf}\left(\frac{1}{2}\Theta qz\right)}{\Theta q}\right].$$

When $ql_t \gg 1$ and $p \ll l_t$, the high-frequency reflectance can be simplified into $$I_{SAA}(q) \rightarrow$$

$$\frac{\mu_b}{2\mu_t}\left[1 + 2 \cdot 6^{1/3}\Gamma\left(\frac{4}{3}\right)\frac{\mu_t}{\mu_s}(l_\Theta q)^{-2/3} - \frac{2}{3}6^{2/3}\Gamma\left(\frac{2}{3}\right)\frac{\mu_t \mu_t'}{\mu_s^2}(l_\Theta q)^{-4/3}\right] \text{ and}$$

-continued $$I_{SAA}(\rho) \rightarrow$$

$$\frac{\mu_b}{2\mu_t}\left[\delta(\rho) + \frac{1}{\pi}\left(\frac{2}{3}\right)^{2/3}\Gamma\left(\frac{2}{3}\right)\frac{\mu_t}{\mu_s}(l_\Theta q)^{-2/3} - \frac{2}{\pi}\left(\frac{2}{3}\right)^{2/3}\Gamma\left(\frac{4}{3}\right)\frac{\mu_t\mu_t'}{\mu_s^2}(l_\Theta q)^{-2/3}\right],$$

wherein $\mu_t' \equiv \mu_a + 2p_b\mu_s$ and the propagation length scale $l_\Theta = \Theta/\mu_s$.

Parameters characterizing the microstructure of the system or a combination of these parameters are/is directly obtained using the high-frequency formulas $I_{SAA}(q)$ and $I_{SAA}(\rho)$ from high-frequency reflection maps of two or more media.

The low-frequency reflectance formulas $$I_{snake}(q) = \frac{\mu_s'^2}{8\pi\beta^2\sqrt{1-q^2\beta^{-2}}}\log\frac{\left(1+\sqrt{1-q^2\beta^{-2}}\right)^2}{1+\sqrt{1-q^4\beta^{-4}}} \text{ and}$$

$$I_{diffuse}(q) = \frac{3\mu_s'^3}{8\pi}\frac{1+(2\beta+Q)z_e}{\beta(\beta+Q)^2(1+Qz_e)}$$

are obtained from the expressions of snake photons and diffuse photons $$I_{snake,diffuse}(\rho) = \frac{\mu_s'^2}{4\pi}\int_0^{+\infty}dz\int_0^{+\infty}dz'\exp[-\beta(z+z')]\times G^{(snake,diffuse)}(r,r').$$

The absorption coefficient and the reduced scattering coefficient are directly obtained using the formula $I_{snake,\,diffuse}(q)$ or $I_{snake,\,diffuse}(\rho)$ from a low-frequency reflection map of one or more media.

In addition, the sub-diffuse scattering light reflectance can be first fitted to obtain the values of $\mu_b/\mu_s$, $\mu_a/\mu_s$ and $\theta/\mu_s$; after the $\mu_b/\mu_s$ is determined, it is supposed that $$g=(1-2p_b)(1-\Theta^2/2)$$

and then the sub-diffuse light and diffuse light reflectance distribution are fitted using least squares fitting to obtain all optical parameters.

The present disclosure includes a turbid medium reflectance calculation method applicable at a random spatial distance and in an entire spatial frequency domain and a method of measuring the reflectance of a turbid medium at high and low spatial frequencies and inverting the obtained light reflectance to obtain optical parameters of the medium. The inversion method may be a table lookup method or a formula fitting method, etc. The measurement of sub-diffuse and diffuse light reflectance of the turbid medium can be used for measuring the optical properties of the turbid medium and microstructures including a phase function and the like in a large area. The phase function of the scattering medium carries basic information about the morphology and optical properties of a single scatterer. In addition, the analysis on the phase function can be used for predicting light propagation and detecting changes or inhomogeneity of microstructures in a random medium. The analysis model proposed by the present disclosure will be extensively and importantly applied in rapid quantification of all optical properties of a scattering medium, including a phase function and the like, especially in the fields of biomedical optics, remote sensing and the like.

DETAILED DESCRIPTION

The embodiments of the present disclosure will be further illustrated below in conjunction with the accompanying drawings.

A collimated beam is incident on an interface of z=0 along the direction $s_{in} \approx \hat{z}$, and passes through a forward peak scattering medium, with a light reflectance of $s_{in} \approx \hat{z}$ in the backscattering direction. In such medium, non-diffuse photons only undergo a few times of large-angle scattering, and are divided into n-order non-diffuse photons according to the times n of large-angle scattering. Since the first-order non-diffuse photons undergo multiple small-angle scattering and one large-angle scattering, the main contribution can be described as a near distance form using small-angle scattering approximation to radiative transfer. The first-order non-diffuse photons are referred to as SAA photons. The second-order non-diffuse photons are referred to as snake photons.

Backscattering of the SAA photons is mainly determined by the diffusion of a forward scattering angle and the backscattering efficiency. It is supposed that the phase function $p(\theta)$ (normalized into $2\pi\int_0^\pi p(\theta)\sin\theta d\theta=1$) of the scattering medium is divided into a forward peak scattering component and an isotropic component, e.g., $$P_{SAA}(\theta)=(1-2p_b)P_{Forward}(\theta)+(2\pi)^{-1}p_b(p_b\ll 1).$$

Figure 1:
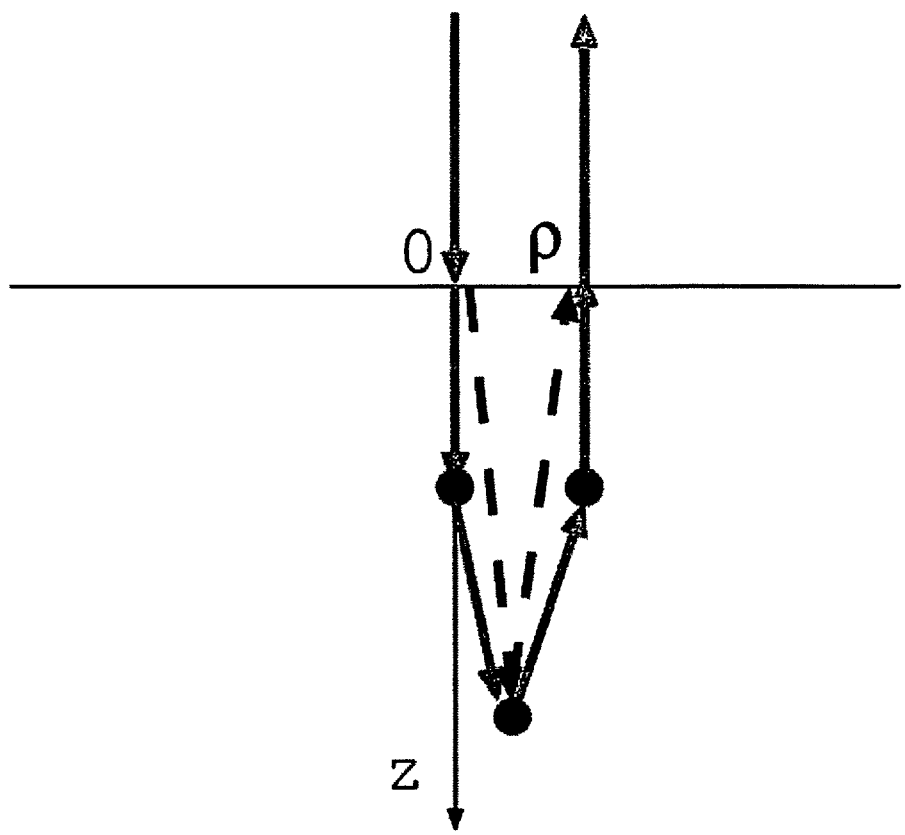
FIG. 1 is a scattering schematic illustration of SAA photons according to the present disclosure.

FIG. 1(a) shows backscattering of first-order non-diffuse photons undergoing multiple small-angle scattering ("red" scatterer) and single large-angle scattering ("blue" scatterer). At the first or last scattering event, the photons can have isotropic scattering (dotted line) and forward peak scattering (solid line) using the probabilities $P_{iso}$ and $1-P_{iso}$ respectively. (b) The introduction of $S^{eff_i}$ improves the precision of SAA photons, and shows the contrast of light reflectance of a suspension of polystyrene spheres having a diameter of 1.5 mm in water based on Monte Carlo simulation.

In a layered medium, the SAA diffusion function for a collimated beam incident at the origin (r=0) in the direction $s_0$ to the depth z is given by the following formula:

$$S(q,z;s_{\perp 0})=\exp(-iq\cdot s_{\perp 0}z)\exp[-\int_0^z \mu t(z-\zeta)d\zeta+\int_0^z \mu s(z-\zeta)\chi(q\zeta,z-\zeta)d\zeta]$$

wherein q is a spatial frequency on the xy plane, $s_{\perp 0}$ is the projection of S0 on the interface, $\mu_t=\mu_s+\mu_a$, in which $\mu_s$ is a scattering coefficient, and $\chi(v, z)$ is two-dimensional Fourier transformation of $(1-2p_b)p_{Forward}(\theta,z)$. The second index item is expanded into $$\exp(-\int_0^z \mu_t(\zeta)d\zeta)[1+\int_0^z \mu_s(z-\zeta)\chi(q\zeta,z-\zeta)d\zeta+\ldots]$$

with a 0-order ballistic item, so that S coming from each scattering orders 0, 1, . . . can be identified.

Then, the reflectance of the SAA photons is obtained, which can be expressed as $$I_{SAA}(q) = \int_0^\infty dz \mu_b(z) \times \left[ S^{eff}(q,z;s_\perp) + \frac{2p_{iso}}{1-p_{iso}} S^{eff\prime}(q,z;s_\perp) \right]. \quad (2)$$

Figure 2:
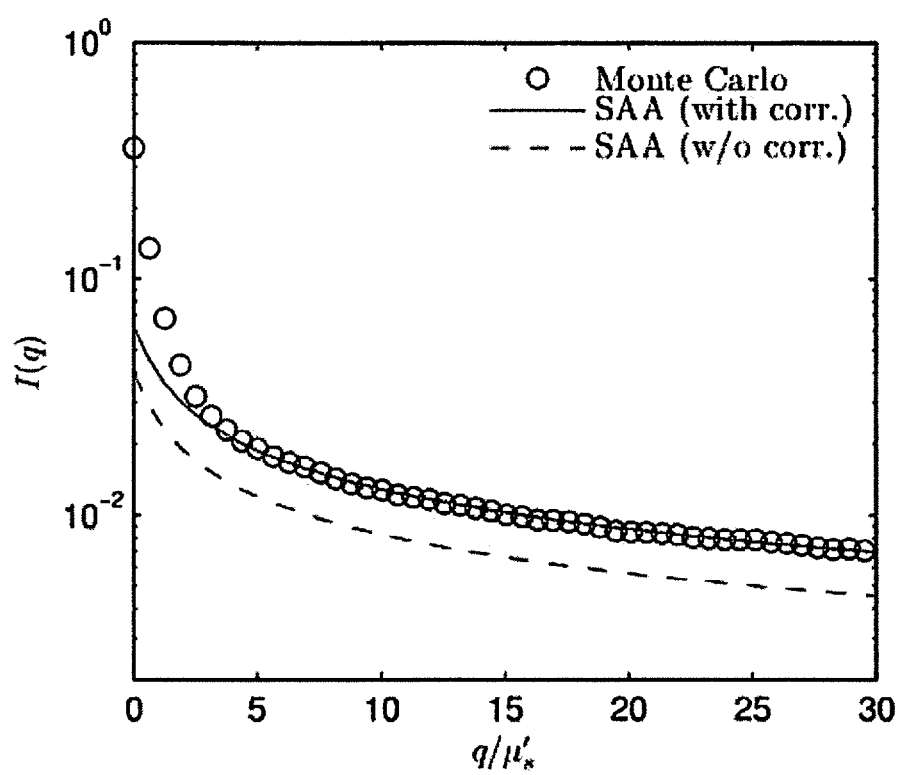
FIG. 2 is a contrast schematic illustration of light reflectance of a suspension of polystyrene spheres having a diameter of 1.5 mm in water based on Monte Carlo simulation.

In the above formula, the backscattering coefficient $\mu_b=\mu_s(z)p(\pi,z)$, $s_\perp=s_{\perp in}+s_{\perp out}$, $S^{eff}$ is a diffusion function for a valid medium with the same phase function and double absorption and scattering, $S^{eff\prime}$ is a diffusion function for a second valid medium with the same phase function and scattering and a absorption coefficient modified to $2\mu_a+2p_b\mu_s$. The second item of formula (2) above indicates that when the photons enter or escape from the medium, they pass through an isotropic scattering path instead of a forward peak scattering path, and the probabilities of the two paths are $P_{iso}$ and $1-P_{iso}(P_{iso}\ll1)$ respectively (see FIG. 1). The introduction of the second item improves the accuracy of SAA (see FIG. 2). It should be noted that the ballistic item should be removed from the $S^{eff}$ to avoid recalculation.

Assuming that $p_{Forward}(\theta)$ satisfies Gaussian distribution, the random phase function $p(\theta)$ of the scattering medium is modified into $$p_{SAA}(\theta) = \frac{1-2p_b}{\pi \Theta^2} \exp\left(-\frac{\theta^2}{\Theta^2}\right) + \frac{1}{2\pi} p_b, \quad (3)$$

from which $$p_b = 2\pi \int_{\pi/2}^\pi p(\theta)\sin\theta d\theta \text{ and}$$

$$\Theta^2 = \frac{2\pi}{1-2p_b} \int_0^\pi p(\theta)\theta^2 \sin\theta d\theta$$

are obtained,

The n-order moment of $P_{SAA}$ is obtained from $$(1-2p_b)\left[1-\frac{n(n+1)}{4}\Theta^2\right].$$

Specifically, the anisotropic factor (n=1) is $$g=(1-2p_b)[1-\Theta^2/2]. \quad (4)$$

Through $p_{iso}=2p_b$ in formula (2), the SAA diffusion function, namely formula (1), is simplified into $$S(q,z;s_{\perp 0}) = \exp(-iq\cdot s_{\perp 0}z)\exp\left[-\mu_t z+(1-2p_b)\mu_s\sqrt{\pi}\frac{\mathrm{erf}\left(\frac{1}{2}\Theta qz\right)}{\Theta q}\right]. \quad (5)$$

Wherein erf is an error function. Compared with the order of other approximate solution truncated phase function moments of radiative transfer, the reflectance (2) of the SAA photons contains the contributions coming from all moments of the phase function.

The expression of $P_{SAA}$ is consistent with a unified Mie and fractal model of light scattering caused by tissues and cells. The Gaussian item captures the contribution from Mie scattering, and the isotropic scattering item is correlated with the refractive index fluctuation of the background. The root mean square scattering angle $\theta$ decreases with the size of the Mie scatterer (large structure) in the tissues and cells.

When $ql_t\gg 1$ and $\rho\ll l_t$, the high-frequency reflectance can be simplified into $$I_{SAA}(q) \rightarrow \quad (6)$$
$$\frac{\mu_b}{2\mu_t}\left[1+2\cdot 6^{1/3}\Gamma\left(\frac{4}{3}\right)\frac{\mu_t}{\mu_s}(l_\Theta q)^{-2/3}-\frac{2}{3}6^{2/3}\Gamma\left(\frac{2}{3}\right)\frac{\mu_t \mu_t'}{\mu_s^2}(l_\Theta q)^{-4/3}\right]$$

and $$I_{SAA}(\rho) \rightarrow \quad (7)$$
$$\frac{\mu_b}{2\mu_t}\left[\delta(\rho)+\frac{1}{\pi}\left(\frac{2}{3}\right)^{2/3}\Gamma\left(\frac{2}{3}\right)\frac{\mu_t}{\mu_s}(l_\Theta q)^{-2/3}-\frac{2}{\pi}\left(\frac{2}{3}\right)^{2/3}\Gamma\left(\frac{4}{3}\right)\frac{\mu_t \mu_t'}{\mu_s^2}(l_\Theta q)^{-2/3}\right],$$

wherein $\mu''=\mu_a+2p_b\mu_s$ and the propagation length scale $l_\Theta\equiv\Theta/\mu_s$.

Parameters characterizing the microstructure of the system or a combination of these parameters are/is directly obtained by inversion using the high-frequency formulas $I_{SAA}(q)$ and $I_{SAA}(\rho)$ from high-frequency reflection maps of two or more media.

The low-frequency reflectance formulas $$I_{snake}(q) = \frac{\mu_s'^2}{8\pi\beta^2\sqrt{1-q^2\beta^{-2}}}\log\frac{\left(1+\sqrt{1-q^2\beta^{-2}}\right)^2}{1+\sqrt{1-q^4\beta^{-4}}} \text{ and}$$

$$I_{diffuse}(q) = \frac{3\mu_s'^3}{8\pi}\frac{1+(2\beta+Q)z_e}{\beta(\beta+Q)^2(1+Qz_e)}$$

are obtained from the expressions of snake photons and diffuse photons $$I_{snake,diffuse}(\rho) = \frac{\mu_s'^2}{4\pi}\int_0^{+\infty}dz\int_0^{+\infty}dz'\exp[-\beta(z+z')]\times G^{(snake,diffuse)}(r,r').$$

In the expression, $\beta\equiv\mu_a+\mu_s'$, $\mu_s'\equiv\mu_s(1-g)$, g is an anisotropic factor, $G^{(snake, diffuse)}$ is a Green's function of snake photons and diffuse photons respectively, $G^{(snake)}(r,r')=\exp(-\beta|r-r'|)/4\pi|r-r'|^2$ is a Green's function of snake photons, and the snake photons are propagated along an isotropic source trajectory in an isotropic scattering turbid medium. In the Fourier domain, the reflectance of the snake photons and the diffuse photons can be simplified into:

$$I_{diffuse}(q) = \frac{3\mu_s'^3}{8\pi} \frac{1+(2\beta+Q)z_e}{\beta(\beta+Q)^2(1+Qz_e)} \text{ and}$$

$$I_{snake}(q) = \frac{\mu_s'^2}{8\pi\beta^2\sqrt{1-q^2\beta^{-2}}} \log\frac{\left(1+\sqrt{1-q^2\beta^{-2}}\right)^2}{1+\sqrt{1-q^4\beta^{-4}}},$$

wherein $Q=\sqrt{q^2+3\mu_a\mu_s'}$, $Z_e$ is an extrapolation length dependent on refractive index mismatch at the interface.

The absorption coefficient and the reduced scattering coefficient can be directly inverted using the formula $I_{snake,\ diffuse}(q)$ or $I_{snake,\ diffuse}(\rho)$ from a low-frequency reflection map of one or more media.

Figure 3:
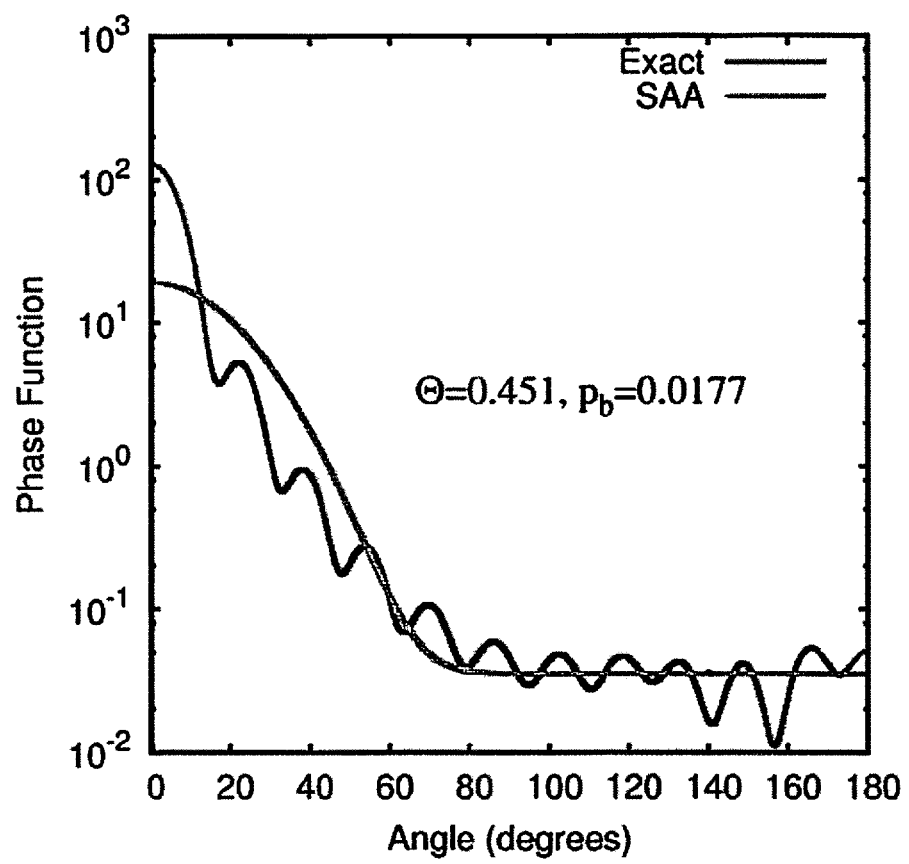
FIG. 3 is a schematic illustration 1 of approximating an exact Mie phase function using an SAA phase function.
Figure 4:
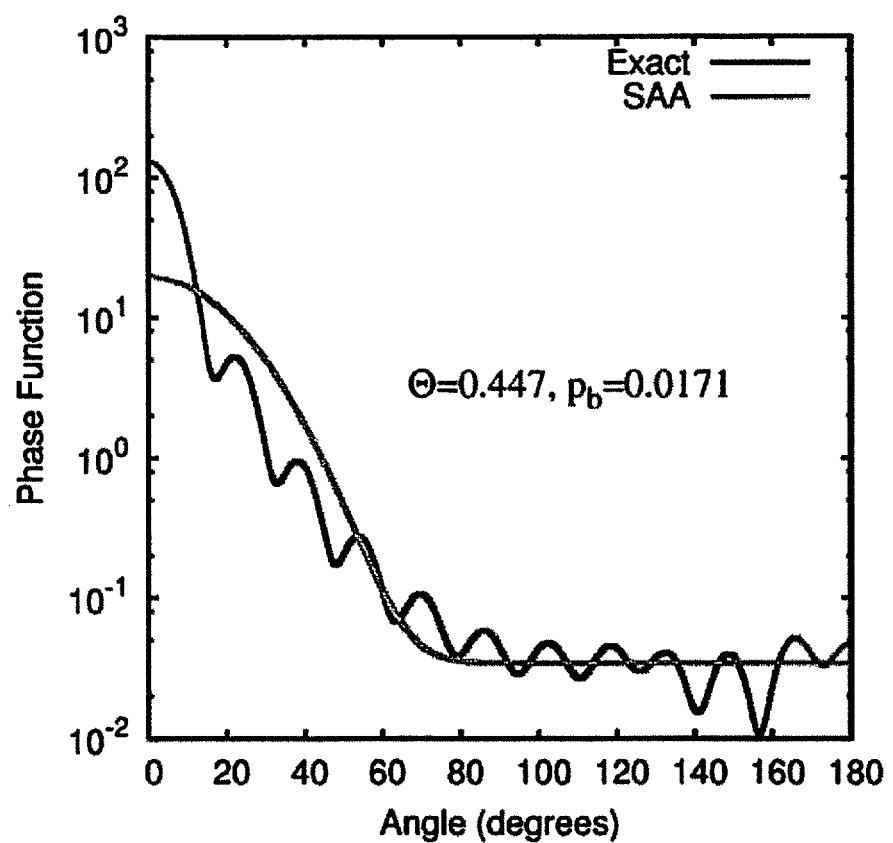
FIG. 4 is a schematic illustration 2 of approximating the exact Mie phase function using the SAA phase function.
Figure 5:
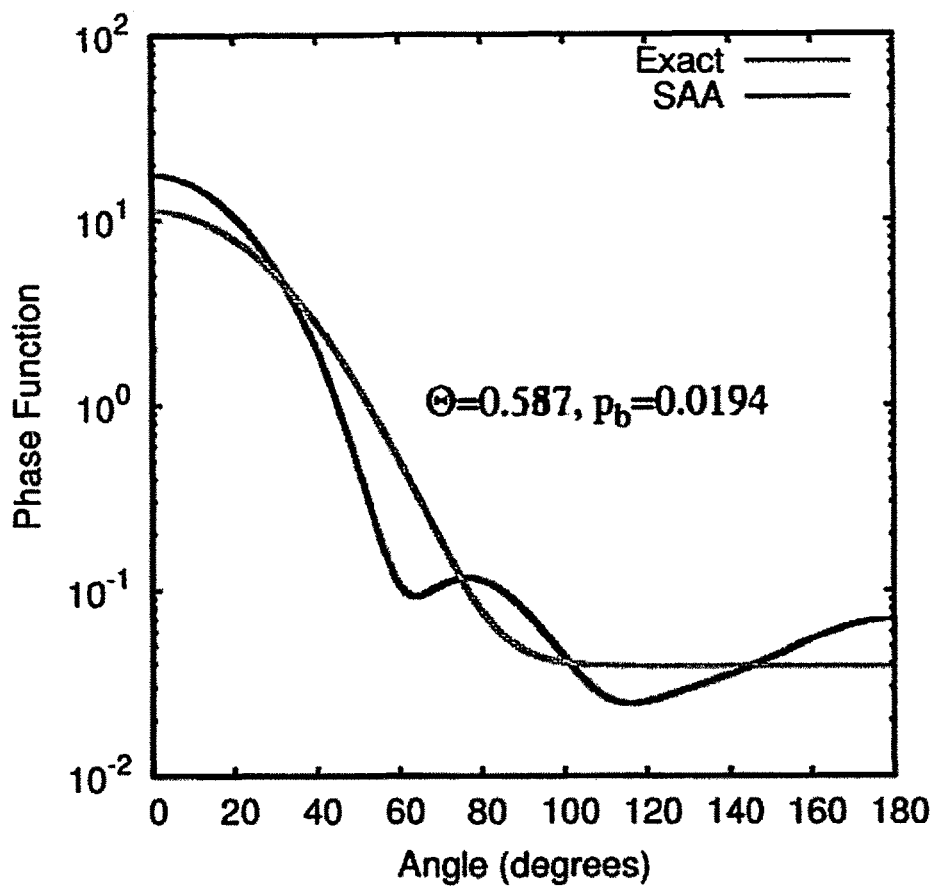
FIG. 5 is a schematic illustration 3 that approximates the exact Mie phase function using the SAA phase function.

FIG. 3, FIG. 4 and FIG. 5 compare the results of simulating the suspension of polystyrene spheres having the diameters of 1.5 μm (not absorbed and absorbed, $\mu_a/\mu_s'=0.16$) and 0.49 μm (not absorbed) in water in a spatial domain and a Fourier domain based on Monte Carlo simulation as well as the light reflectance of SAA photons, snake photons and diffuse photons.

In the Monte Carlo simulation, the total number of incident photons is set to 106, assuming that the semi-infinite medium is matched with the surrounding refractive index. Absorption of the scattering medium is achieved by adding a non-zero imaginary part to the refractive index of the polystyrene particles. The parameters corresponding to the SAA photons are $p_b=0.0177$ and $\Theta=0.451$, $p_b=0.0171$ and $\Theta=0.447$, $p_b=0.0194$ and $\Theta=0.587$, respectively.

Figure 6:
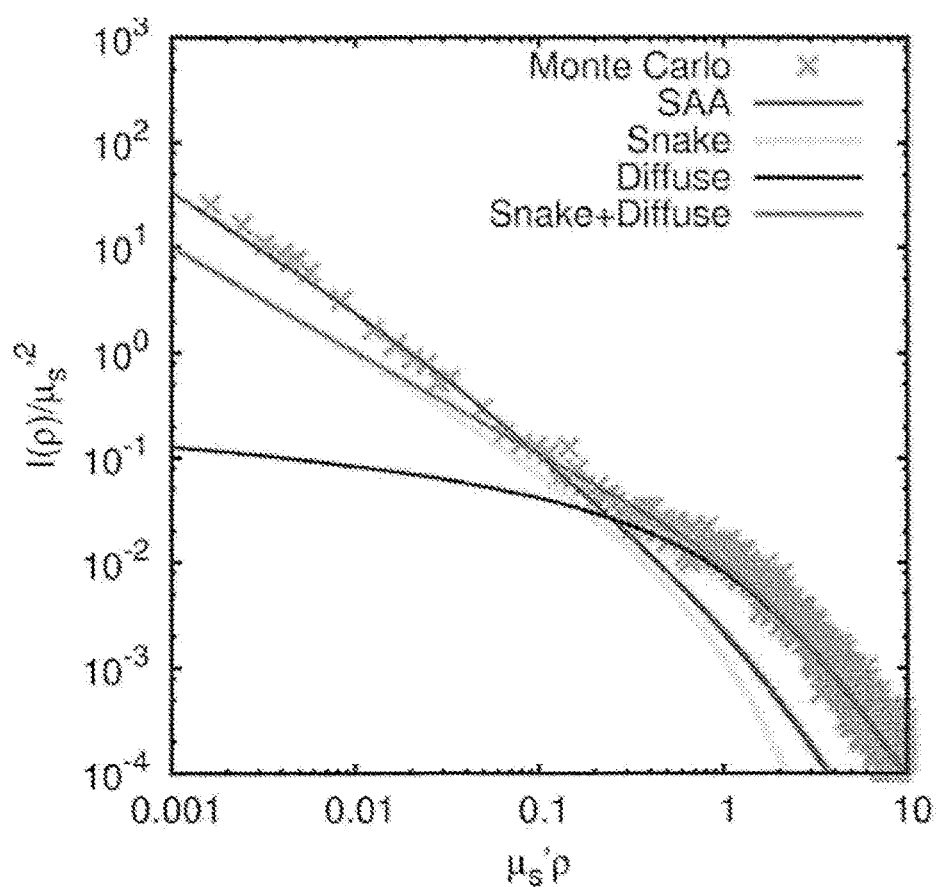
FIG. 6 is a schematic illustration 1 of spatial distribution of reflectance of parallel beams perpendicularly incident at an origin at a radial position r away from the origin.
Figure 7:
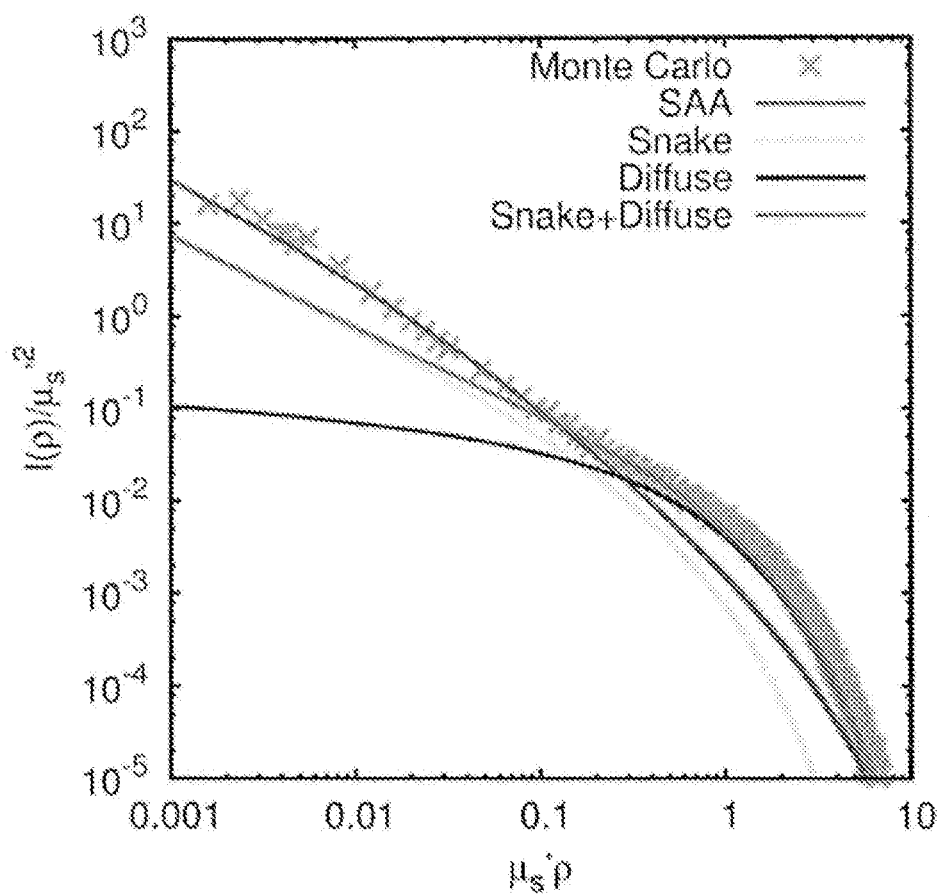
FIG. 7 is a schematic illustration 2 of spatial distribution of reflectance of parallel beams perpendicularly incident at the origin at the radial position r away from the origin.
Figure 8:
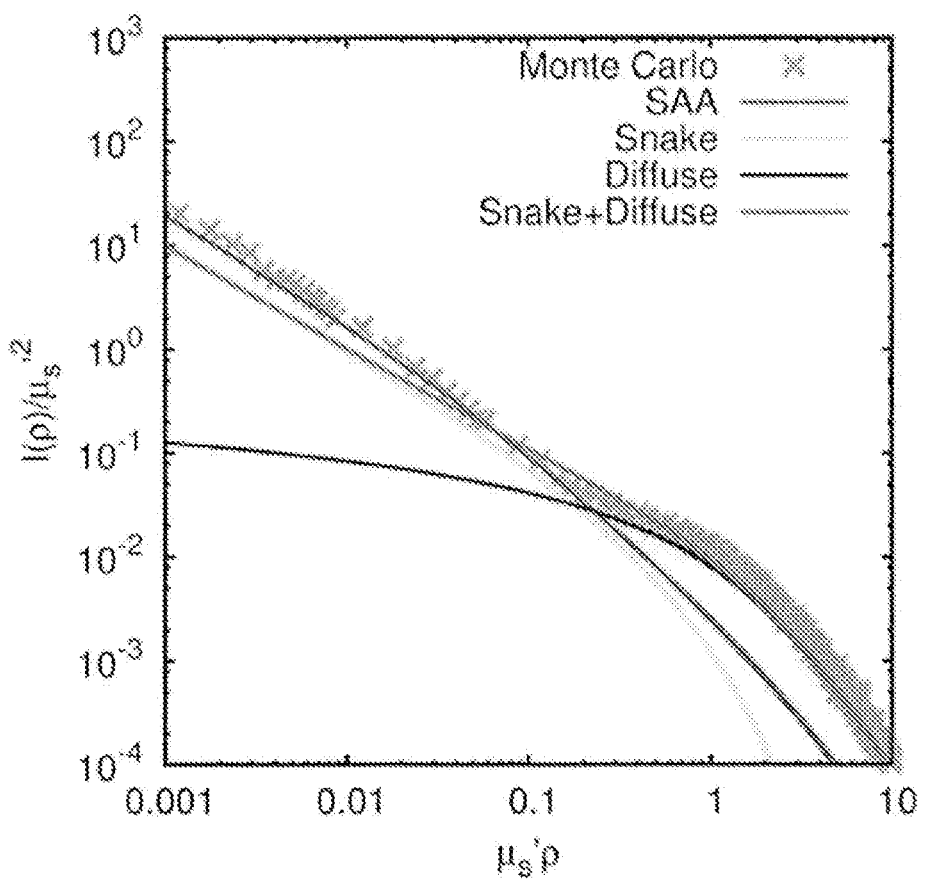
FIG. 8 is a schematic illustration 3 of spatial distribution of reflectance of parallel beams perpendicularly incident at the origin at the radial position r away from the origin.

FIG. 6, FIG. 7 and FIG. 8 compare the reflectance of SAA photons, and snake and diffuse photons and the results of simulating the suspension of polystyrene spheres having the diameters of 1.5 μm (FIG. 6: not absorbed, FIG. 7: $\mu_a/\mu_s'=0.16$; g=0.92) and 0.49 μm (FIG. 8: not absorbed, g=0.86) in water based on Monte Carlo simulation. The wavelength of incident light is 0.515 μm.

Figure 9:
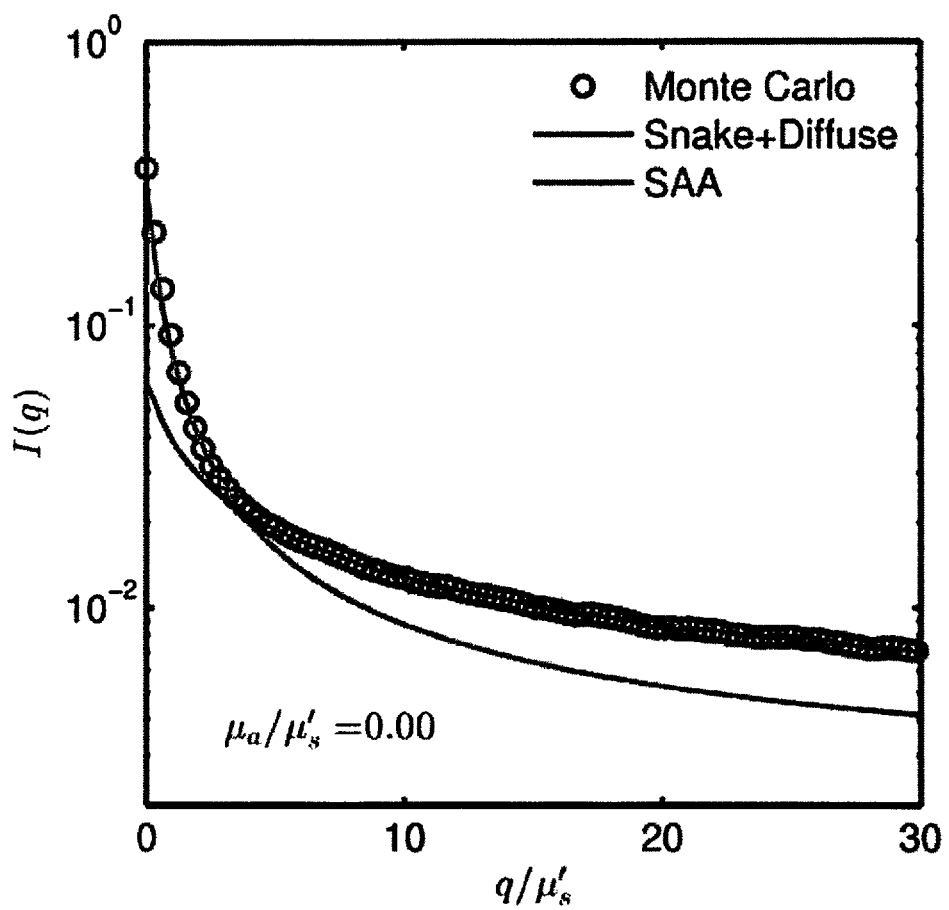
FIG. 9 is a schematic illustration 1 of reflectance of normal-incidence spatial modulated plane waves at a spatial frequency q.
Figure 10:
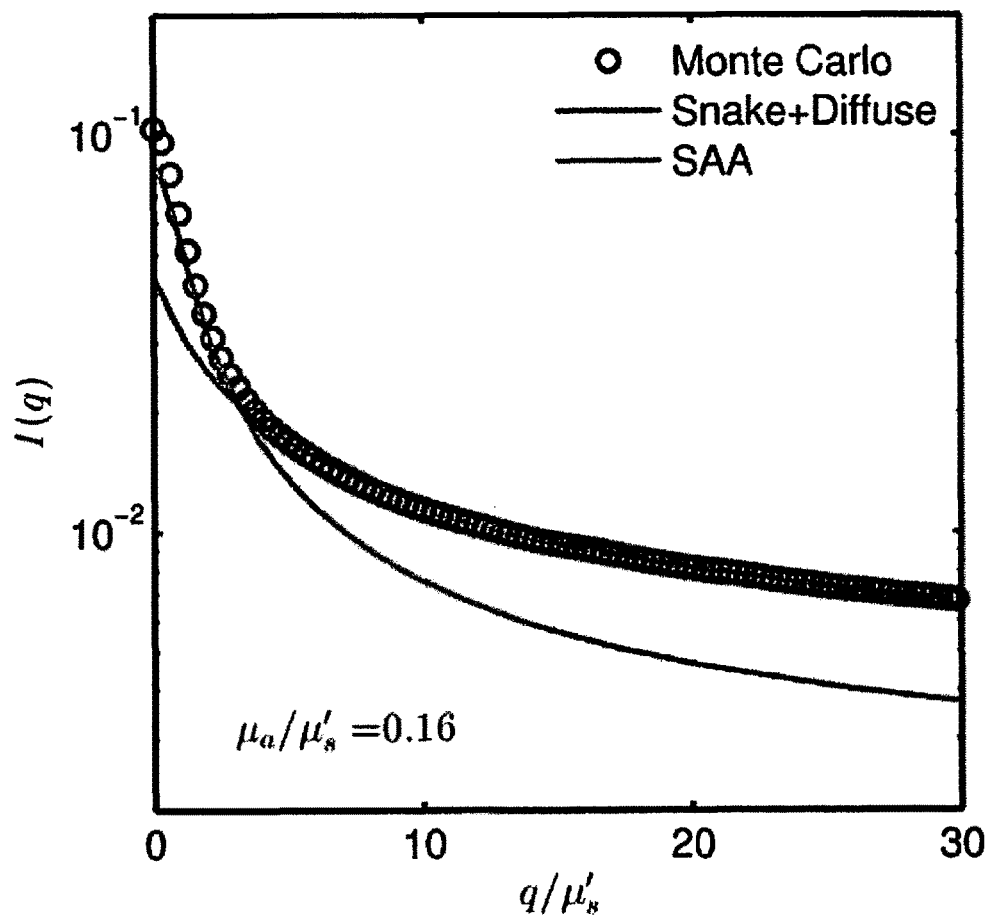
FIG. 10 is a schematic illustration 2 of reflectance of normal-incidence spatial modulated plane waves at the spatial frequency q.
Figure 11:
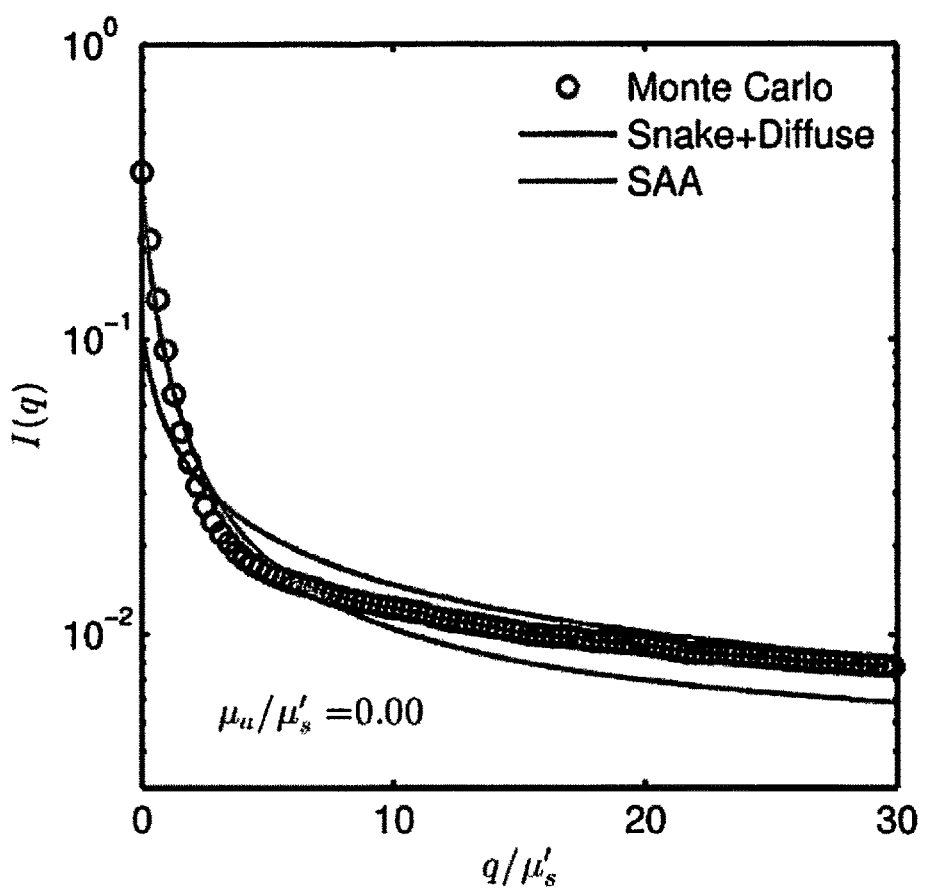
FIG. 11 is a schematic illustration 3 of reflectance of normal-incidence spatial modulated plane waves at the spatial frequency q.

FIG. 3 to FIG. 5 show using the SAA phase function to approximate the exact Mie phase function. FIG. 6 to FIG. 8 show the spatial distribution of reflectance of parallel beams perpendicularly incident at an origin at a radial position r away from the origin. FIG. 9, FIG. 10 and FIG. 11 show the reflectance of normal-incidence spatial modulated plane waves at a spatial frequency q.

| | $d = 1.50$ μm, $\mu_a = 0$ | $d = 1.50$ μm, $\mu_a = 0.16\mu_s'$ | $d = 0.49$ μm, $\mu_a = 0$ |
|---|---|---|---|
| $R^2$ | 0.9915 | 0.9877 | 0.9668 |

TABLE 1

Matching relation between polystyrene sphere suspension model (diameter d, absorption coefficient $\mu_a = 0$) and Monte Carlo simulation. $R^2 = 1$ indicates the similarity between the model and the real value.

| | $\mu_s$ (cm$^{-1}$) | $\mu_a$ (cm$^{-1}$) | g | $p_b$ | $\Theta$ | $\mu_b$ (cm$^{-1}$) |
|---|---|---|---|---|---|---|
| Theoretical | 1.000 | 0.0130 | 0.921 | 0.0173 | 0.447 | 0.00388 |
| Fitted | 1.019 | 0.0116 | 0.915 | 0.0204 | 0.431 | 0.00331 |

Table 2, Comparison of parameters fitted by Monte Carlo simulation on the light reflectance of polystyrene sphere suspension (d=1.5 μm, $\mu_a/\mu_s'=0.16$) and theoretical values.

The SAA photons and the combined snake and diffuse scattering photons well describe the reflectance of a light source and a detector in a real space over short and long distances (FIGS. 6-8), and the reflectance in a frequency domain at high and low spatial frequencies (FIG. 9-11).

When the distance is greater than $\beta^{-1}$, this division on the backscattering light is consistent with the general radial distribution independent from the specific form of a phase function. Formula (8) perfectly describes the light reflectance of a forward peak scattering medium with low and medium absorption ($\mu_a/\mu_s'<1$). Table 1 shows the similarity calculated within $0\leq q/\mu_s'\leq 100$ between the Fourier space model and the Monte Carlo simulation. The similarity between the model and the Monte Carlo simulation is defined as follows $$R^2 = 1 - \frac{SSR}{SST},$$

wherein SSR=$\Sigma(\log I_{modal}-\log I_{MC})^2$ is a mean square error of the model, SST=$\Sigma(\log I_{MC}-\overline{\log I_{MC}})^2$ is a true value deviation, $\overline{\log I_{MC}}$ is the mean of log $I_{MC}$. $R^2$ indicates perfect overlap matching of the model and the true value. The similarity value is calculated within the range $0\leq q/\mu_s'\leq 100$ in the Fourier space. When the absorption increases ($\mu_a/\mu_s'\approx 1$), the photons are no longer completely randomized in the propagation direction thereof or the light is no longer scattered toward forward peaks in the medium, and the precision of formula (8) decreases.

The closed form of the light reflectance is:

$$I(q) = \begin{cases} I_{snake}(q) + I_{diffuse}(q) + \mu_b/2\mu_t & q < q_c \\ I_{SAA}(q) & q > q_c \end{cases}. \quad (8)$$

Figure 12:
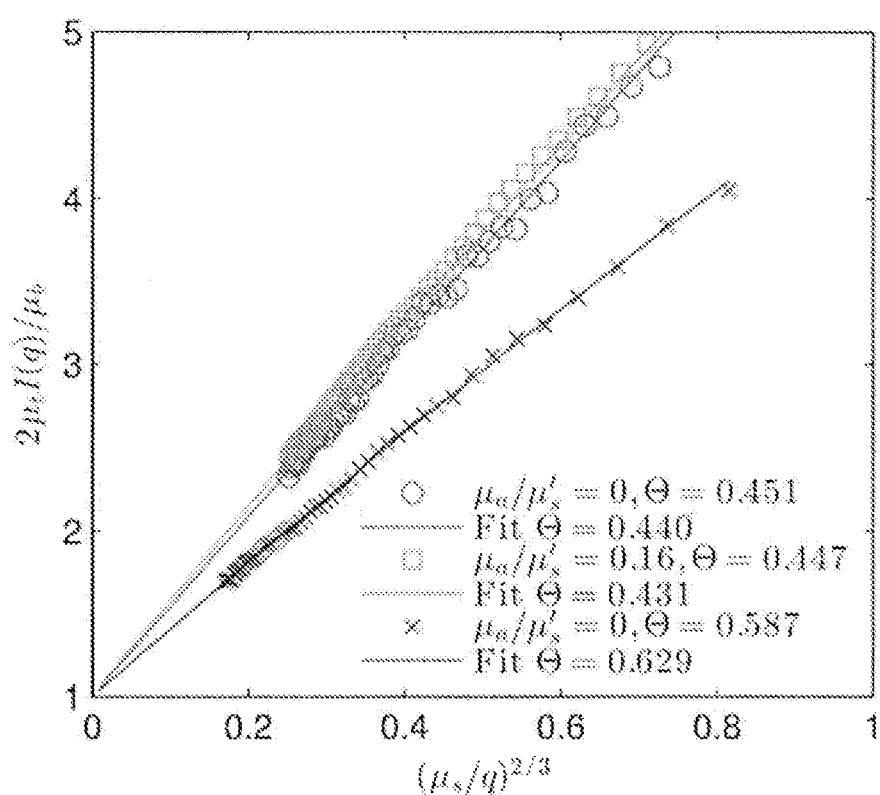
FIG. 12 is a schematic illustration of a result of fitting the polystyrene suspension shown in FIG. 2 through the formula $I_{SAA}(q)$.

The closed form (8) of the light reflectance and the limiting forms (6) and (7) show, in addition to well-known transfer mean free path $l_t=1/(1-g)\mu_s$ acting on light diffusion and reflectance at low spatial frequencies (long distance), there is a new propagation length scale $l_\Theta=\Theta/\mu_s$ characterizing the reflectance of sub-diffuse light at high spatial frequencies (short distance), which is determined only by the angle width of the forward peak portion of the phase function. For the forward peak scattering medium, an internal relation between the above two dimensions can be further established through formula (4), and approximately satisfies $\mu_s^3 l_t l_\Theta^2=2$. The high-frequency (short distance) light reflectance can be conveniently measured through formulas (6, 7). FIG. 12 shows the results of fitting the polystyrene suspension shown in FIG. 3 to FIG. 11 through formula (6). The diffusion angle $\Theta$ of the scattering light is determined by the precision of 2.4%, 3.6% and 5.6%, respectively.

A complete group of optical properties of the turbid medium is determined by fitting the light reflectance at low and high spatial frequencies, and the group of optical properties include an SAA phase function defined entirely by the diffusion angle $\Theta$ of the scattering light, an isotropic scattering background $p_b$ of a random phase function of a scattering medium, a backscattering coefficient $\mu_b$, a scattering coefficient $\mu_s$, an absorption coefficient $\mu_a$ and an anisotropic factor g.

For example, table 2 shows the parameter results of fitting the light reflectance of polystyrene suspension (d=1.5 μm, $\mu_a/\mu_s'$=0.16) based on Monte Carlo simulation.

In addition, the sub-diffuse scattering light reflectance can be first fitted to obtain the values of $\mu_b/\mu_s$, $\mu_a/\mu_s$ and $\Theta/\mu_s$, $g=(1-2p_b)(1-\Theta^2/2)$ is assumed after the $\mu_b/\mu_s$ is determined, and then the sub-diffuse light and the diffuse light reflectance distribution are fitted using least squares fitting to obtain all optical parameters.

The group of optical parameters obtained from the light reflectance agree well with the theoretical values. In particular, the precision of the extracted scattering characteristics and phase function parameters ($\mu$, $g$, $\Theta$) is very good, partly because of the constraints between $g$ and $\Theta$. $g$ and $\Theta$ characterize the diffuse scattering and sub-diffuse scattering light reflectance caused by the forward peak scattering medium, respectively.

In summary, the present disclosure proposes a reflectance analysis model describing a forward peak scattering medium at a random light source and detector distance, and its application in analyzing the optical parameters and phase functions of the forward peak scattering medium. When the absorption is at medium to low levels, the analysis model shows excellent performance over the entire spatial scale, and it has been successfully proved that the model can be applied to accurately determine the optical properties and phase functions of the turbid medium from the sub-diffuse and diffuse light reflectance of the medium. The phase function of the scattering medium carries basic information about the morphology and the optical properties of a single scatterer. In addition, the analysis on the phase function can also be used for predicting light propagation and detecting the changes or inhomogeneities of microstructures in a random medium. With the development of spatial modulated illumination in recent years, it has become possible to quickly measure the reflectance of sub-diffuse and diffuse scattering light in a wide field of view. Therefore, the analysis model proposed by the present disclosure will be extensively and importantly applied in rapid quantification of all optical properties of a scattering medium, including a phase function and the like, especially in the fields of biomedical optics, remote sensing and the like.

The invention claimed is:

1. A light reflection imaging method for acquiring optical parameters and microstructures of tissues in a large area, comprising:

directing a collimated beam of light at a forward peak scattering medium;

detecting a first order non-diffuse photon in a backscattered direction;

detecting a second order non-diffuse photon in the backscattered direction;

detecting a diffuse photon in the backscattered direction;

determining a low-frequency reflectance formula $$I_{snake}(q)+I_{diffuse}(q)+\mu_b/2\mu_t$$

and a high-frequency reflectance formula $$I_{SAA}(q),$$

according to $$I(q) = \begin{cases} I_{snake}(q) + I_{diffuse}(q) + \mu_b/2\mu_t & q < q_c \\ I_{SAA}(q) & q > q_c \end{cases},$$

wherein $q_c \sim 2\pi\beta$;

determining an absorption coefficient $\mu_a$ and a reduced scattering coefficient $\mu_s'$ from the reflectance determined by applying the low-frequency reflectance formula and an inversion method in sequence; and determining an anisotropic factor $g$, a propagation length scale $l_\Theta$ and an isotropic scattering background $p_b$ of a random phase function of the forward peak scattering medium determined by applying the high-frequency reflectance formula and the inversion method.

2. The light reflection imaging method for acquiring optical parameters and microstructures of tissues in a large area according to claim 1, wherein the inversion method is a table lookup method or a formula fitting method.

3. The light reflection imaging method for acquiring optical parameters and microstructures of tissues in a large area according to claim 1, wherein a high-frequency reflectance formula $$I_{SAA}(q) = \int_0^\infty dz\mu_b(z) \times \left[S^{eff}(q,z;s_\perp) + \frac{2p_{iso}}{1-p_{iso}}S^{eff}(q,z;s_\perp)\right]$$

is obtained from an SAA diffusion function $$S(q,z;s_{\perp 0})=\exp(-iq\cdot s_{\perp 0}z)\exp[-\int_0^z\mu_t(z-\zeta)d\zeta+\int_0^z\mu_b(z-\zeta)\chi(q\zeta,z-\zeta)d\zeta].$$

4. The light reflection imaging method for acquiring optical parameters and microstructures of tissues in a large area according to claim 3, wherein, assuming that $p_{Forward}(\theta)$ satisfies Gaussian distribution, the random phase function $p(\theta)$ of the scattering medium is modified into:

$$p_{SAA}(\theta) = \frac{1-2p_b}{\pi\Theta^2}\exp\left(-\frac{\theta^2}{\Theta^2}\right) + \frac{1}{2\pi}p_b,$$

from which $$p_b = 2\pi\int_{\pi/2}^\pi p(\theta)\sin\theta d\theta$$

and $$\theta^2 = \frac{2\pi}{1-2p_b}\int_0^\pi p(\theta)\theta^2\sin\theta d\theta$$

are determined, and through $p_{iso}=2p_b$, the SAA diffusion function is transformed into $$S(q,z;s_{\perp 0}) = \exp(-iq\cdot s_{\perp 0}z)\exp\left[-\mu_t z + (1-2p_b)\mu_s\sqrt{\pi}\frac{\text{erf}\left(\frac{1}{2}\Theta qz\right)}{\Theta q}\right].$$

5. The light reflection imaging method for acquiring optical parameters and microstructures of tissues in a large area according to claim 3, wherein when $ql_t\gg 1$ and $p\ll l_t$, the high-frequency reflectance can be simplified into $$I_{SAA}(q) \to \frac{\mu_b}{2\mu_t}\left[1 + 2\cdot 6^{1/3}\Gamma\left(\frac{4}{3}\right)\frac{\mu_t}{\mu_s}(l_\Theta q)^{-2/3} - \frac{2}{3}6^{2/3}\Gamma\left(\frac{2}{3}\right)\frac{\mu_t\mu_t'}{\mu_s^2}(l_\Theta q)^{-4/3}\right]$$

and

-continued $$I_{SAA}(\rho) \to \frac{\mu_b}{2\mu_t}\left[\delta(\rho) + \frac{1}{\pi}\left(\frac{2}{3}\right)^{2/3}\Gamma\left(\frac{2}{3}\right)\frac{\mu_t}{\mu_s}(l_\Theta q)^{-2/3} - \frac{2}{\pi}\left(\frac{2}{3}\right)^{2/3}\Gamma\left(\frac{4}{3}\right)\frac{\mu_t\mu_t'}{\mu_s^2}(l_\Theta q)^{-2/3}\right],$$

wherein $\mu_t'=\mu_a+2p_b\mu_s$ and the propagation length scale $l_\Theta=\Theta/\mu_s$.

6. The light reflection imaging method for acquiring optical parameters and microstructures of tissues in a large area according to claim 5, wherein parameters characterizing the microstructure of the system or a combination of these parameters are/is directly obtained using the high-frequency formulas $I_{SAA}$ (q) and $I_{SAA}$ (ρ) from high-frequency reflection maps of two or more media.

7. The light reflection imaging method for acquiring optical parameters and microstructures of tissues in a large area according to claim 1, wherein the low-frequency reflectance formulas $$I_{snake}(q) = \frac{\mu_s'^2}{8\pi\beta^2\sqrt{1-q^2\beta^{-2}}}\log\frac{\left(1+\sqrt{1-q^2\beta^{-2}}\right)^2}{1+\sqrt{1-q^4\beta^{-4}}} \text{ and}$$

$$I_{diffuse}(q) = \frac{3\mu_s'^3}{8\pi}\frac{1+(2\beta+Q)z_e}{\beta(\beta+Q)^2(1+Qz_e)}$$

are obtained from the expressions of snake photons and diffuse photons $$I_{snake,diffuse}(\rho) = \frac{\mu_s'^2}{4\pi}\int_0^{+\infty}dz\int_0^{+\infty}dz'\exp[-\beta(z+z')]\times G^{(snake,diffuse)}(r,r').$$

8. The light reflection imaging method for acquiring optical parameters and microstructures of tissues in a large area according to claim 7, wherein the absorption coefficient and the reduced scattering coefficient are directly obtained using the formula $I_{snake,\ diffuse}$(q) or $I_{snake,\ diffuse}$(ρ) from a low-frequency reflection map of one or more media.

9. The light reflection imaging method for acquiring optical parameters and microstructures of tissues in a large area according to claim 1, wherein in addition, the sub-diffuse scattering light reflectance can be first fitted to obtain the values of $\mu_b/\mu_s$, $\mu_a/\mu_s$ and $\Theta/\mu_s$; after the $\mu_b/\mu_s$ is determined, it is supposed that $$g=(1-2p_b)(1-\Theta^2/2);$$

and then the sub-diffuse light and diffuse light reflectance distribution is fitted using least squares fitting to obtain all optical parameters.

* * * * *